United States Patent [19]

Sredni et al.

[11] Patent Number: 5,610,179
[45] Date of Patent: Mar. 11, 1997

[54] METHOD OF TREATING BABESIOSIS

[76] Inventors: Benjamin Sredni, Shachal 3 Street, Kfar-Saba; Michael Albeck, 8 Harel Street, 52444 Ramat-Gan, both of Israel

[21] Appl. No.: 357,129

[22] Filed: Dec. 15, 1994

[51] Int. Cl.$^6$ .............. A61K 31/335; A61K 31/35; A61K 31/34; A61K 33/24
[52] U.S. Cl. .............. 514/450; 514/451; 514/452; 514/461; 514/463; 424/650; 424/702
[58] Field of Search .............. 514/450, 451, 514/452, 461, 463, 475, 449; 424/702, 650

[56] References Cited

U.S. PATENT DOCUMENTS 4,761,490  8/1988  Albeck et al. .............. 549/347

*Primary Examiner*—John W. Rollins
*Attorney, Agent, or Firm*—Hedman, Gibson & Costigan, P.C.

[57] ABSTRACT

A method of treating or preventing babesiosis is described which is based on the administration of a tellurium compound. The preferred tellurium compound is ammonium trichloro (O,O'-dioxoethylene tellurate).

10 Claims, 10 Drawing Sheets

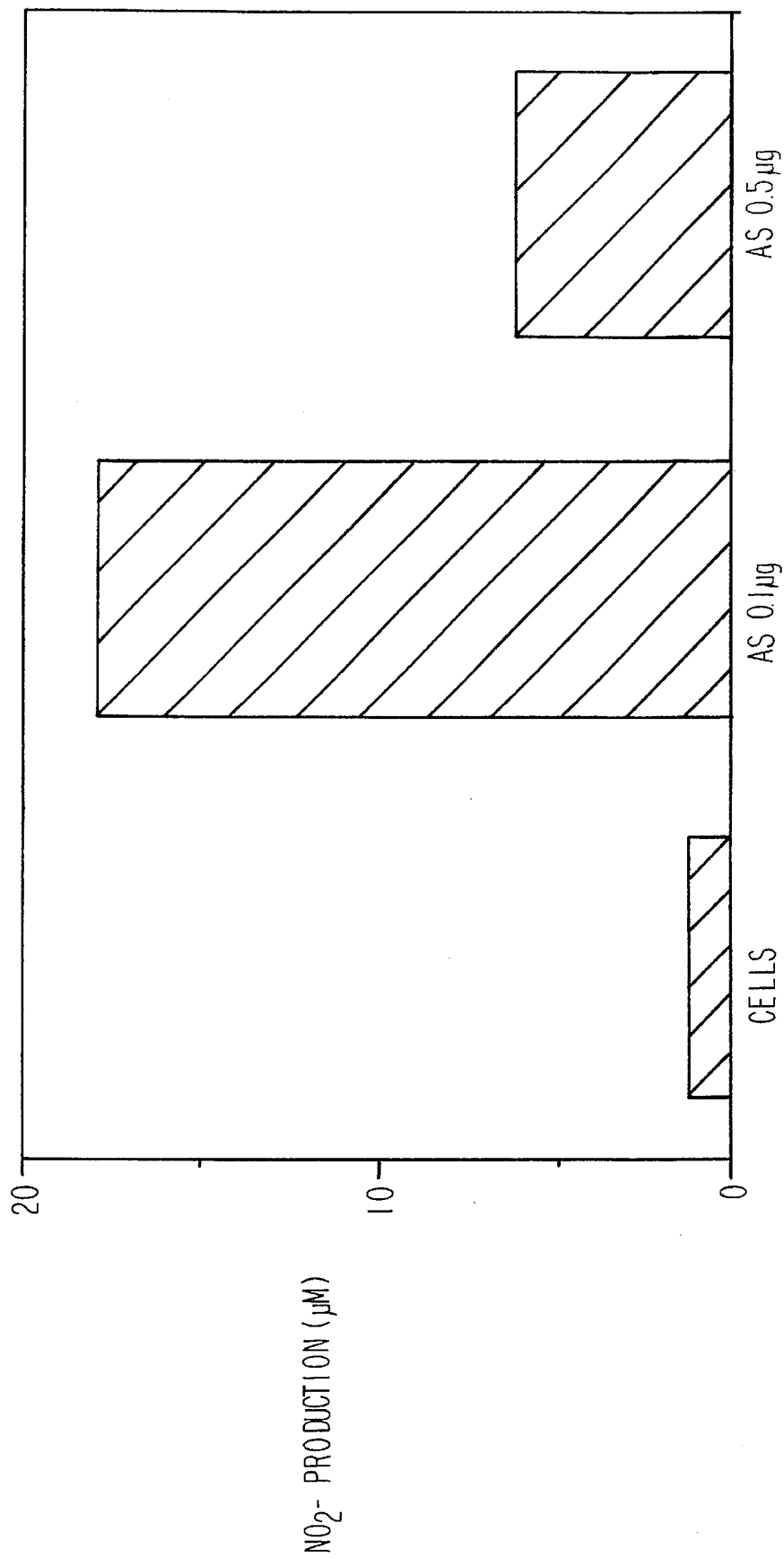

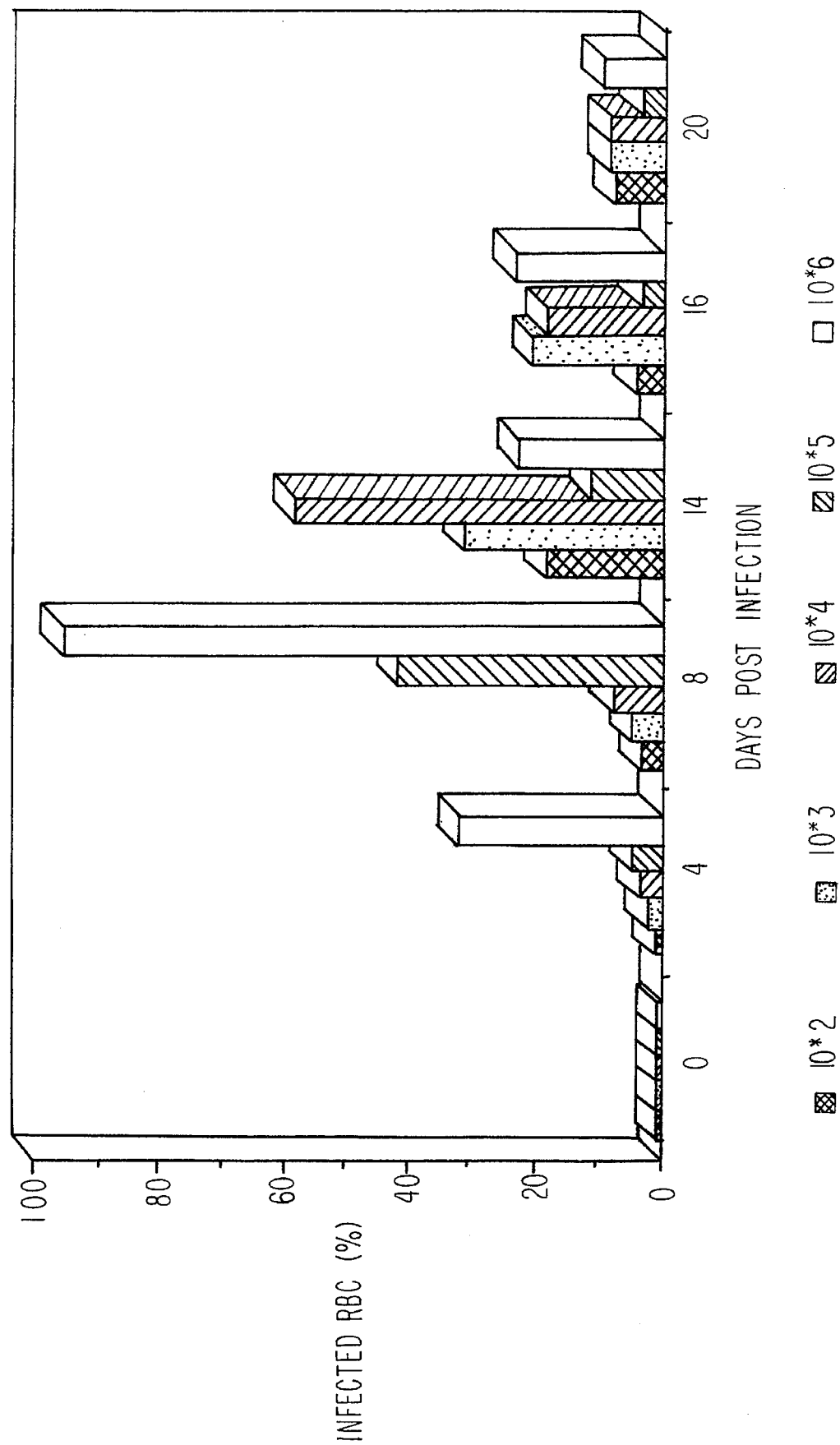

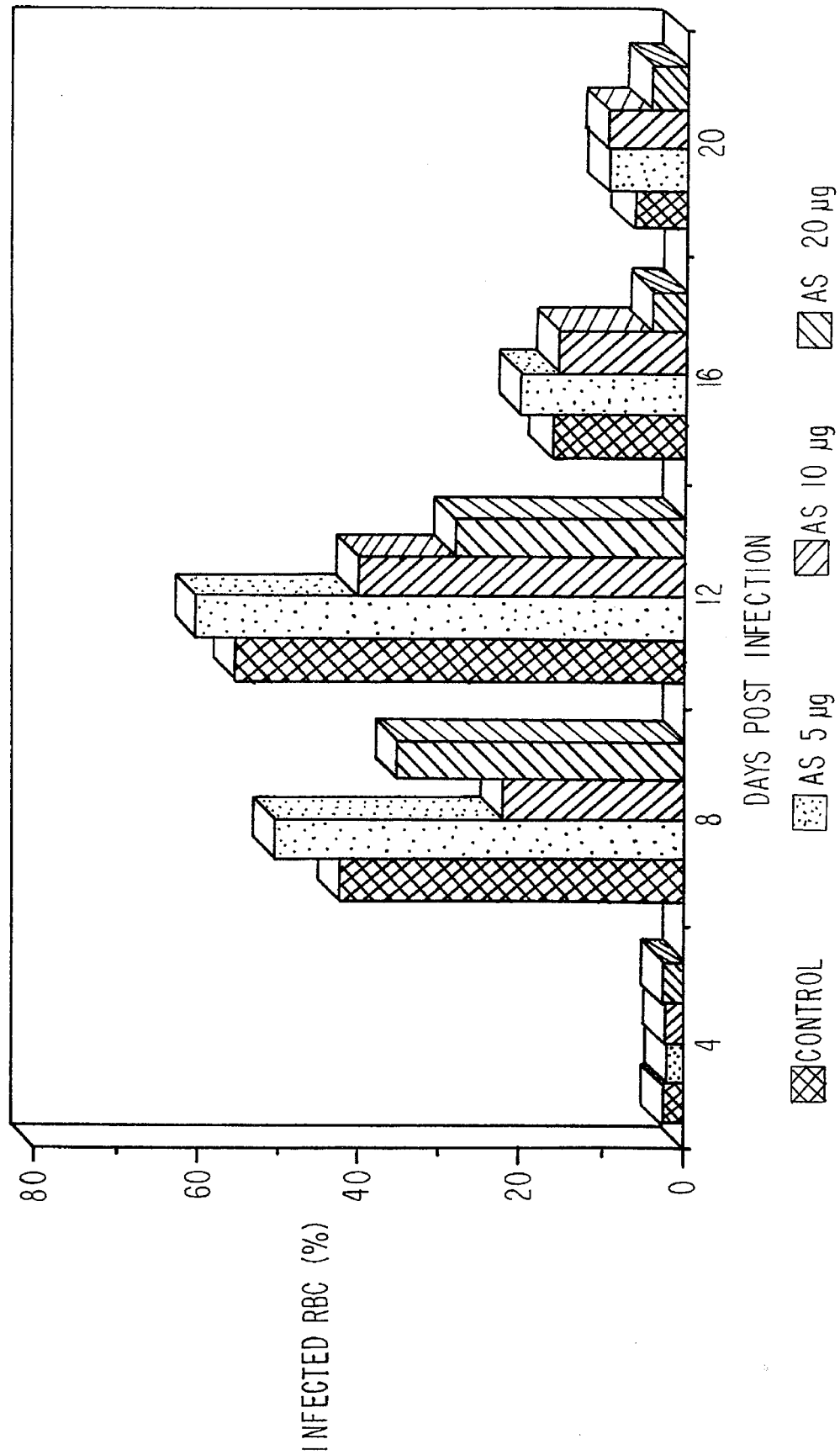

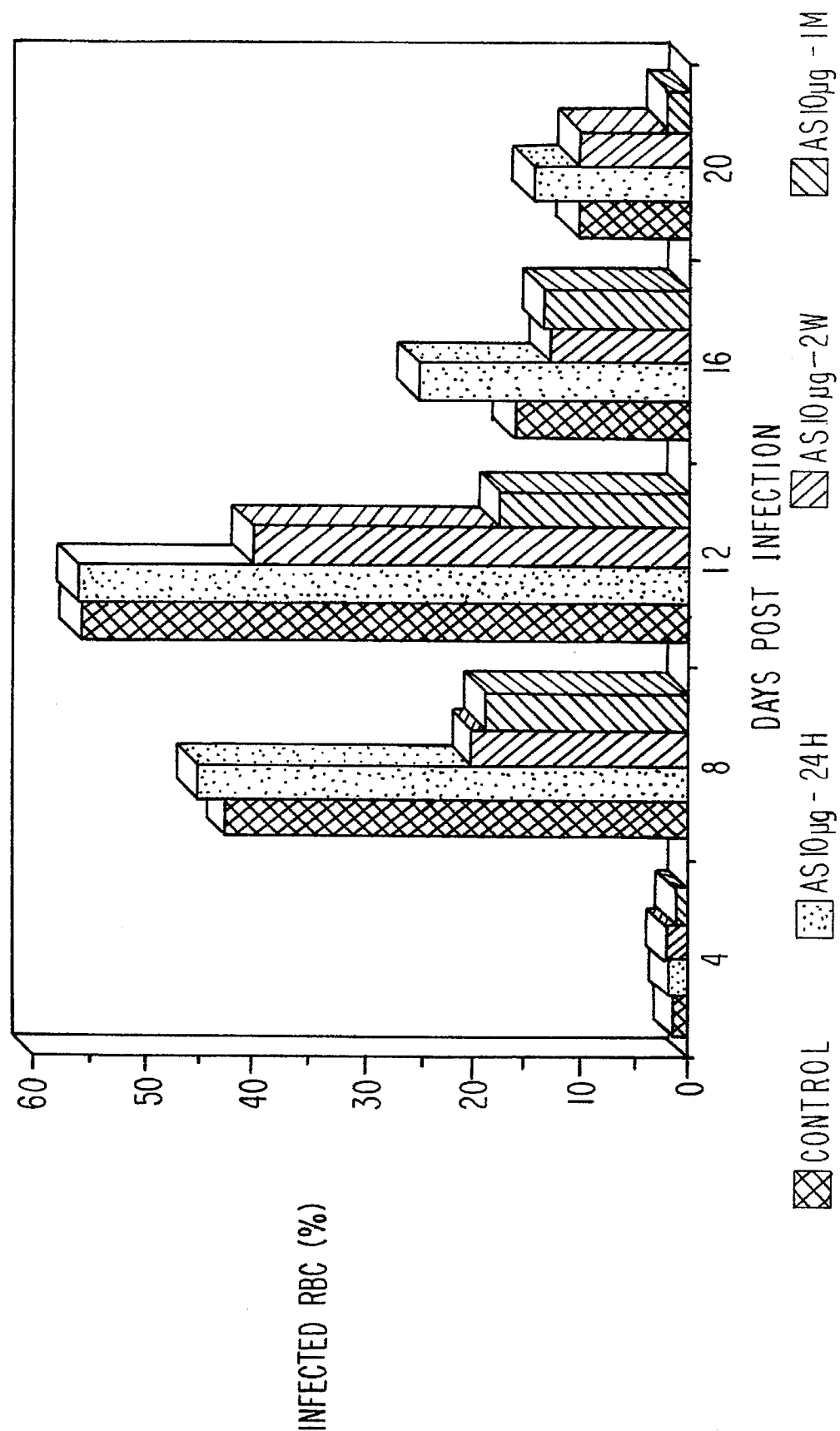

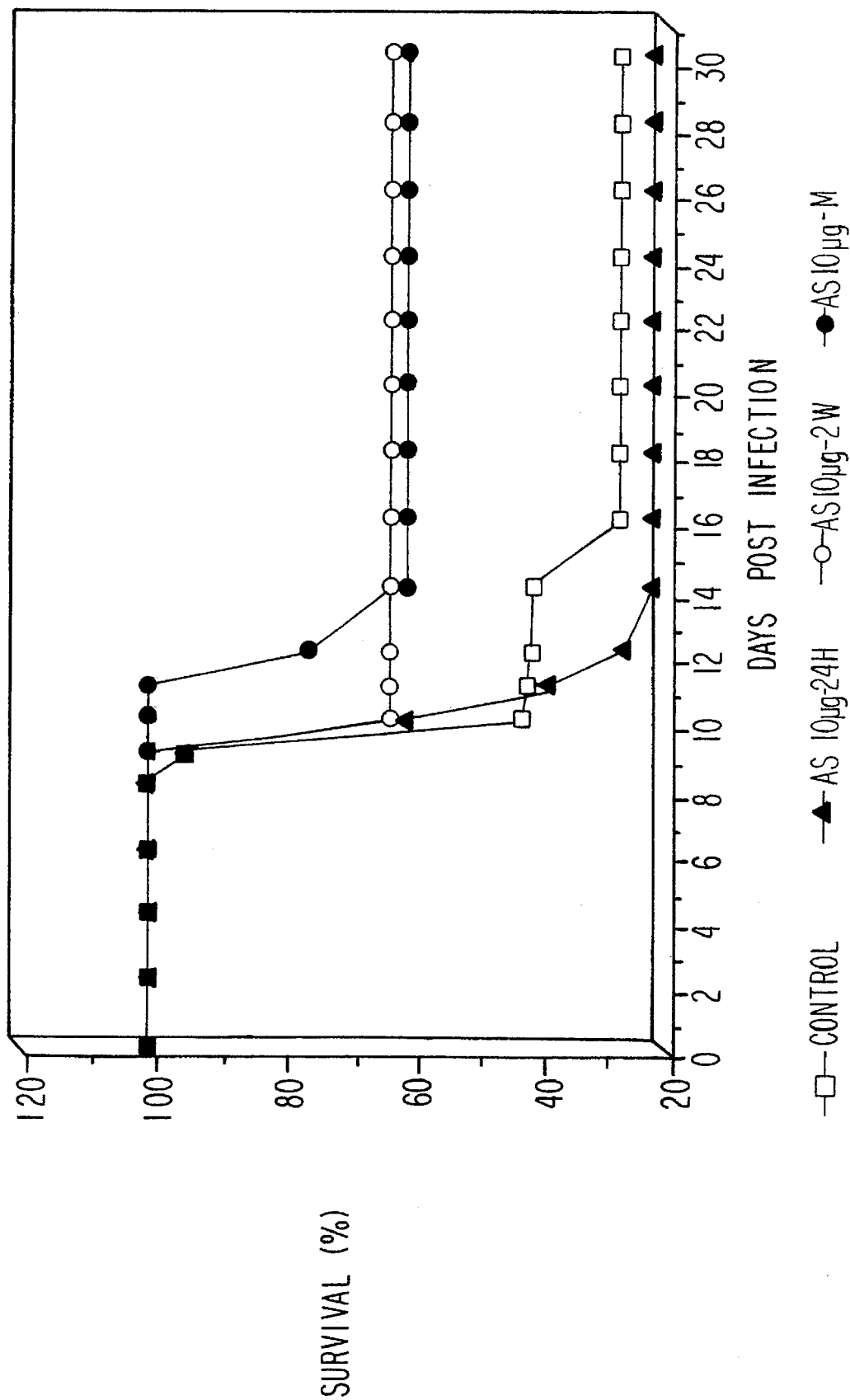

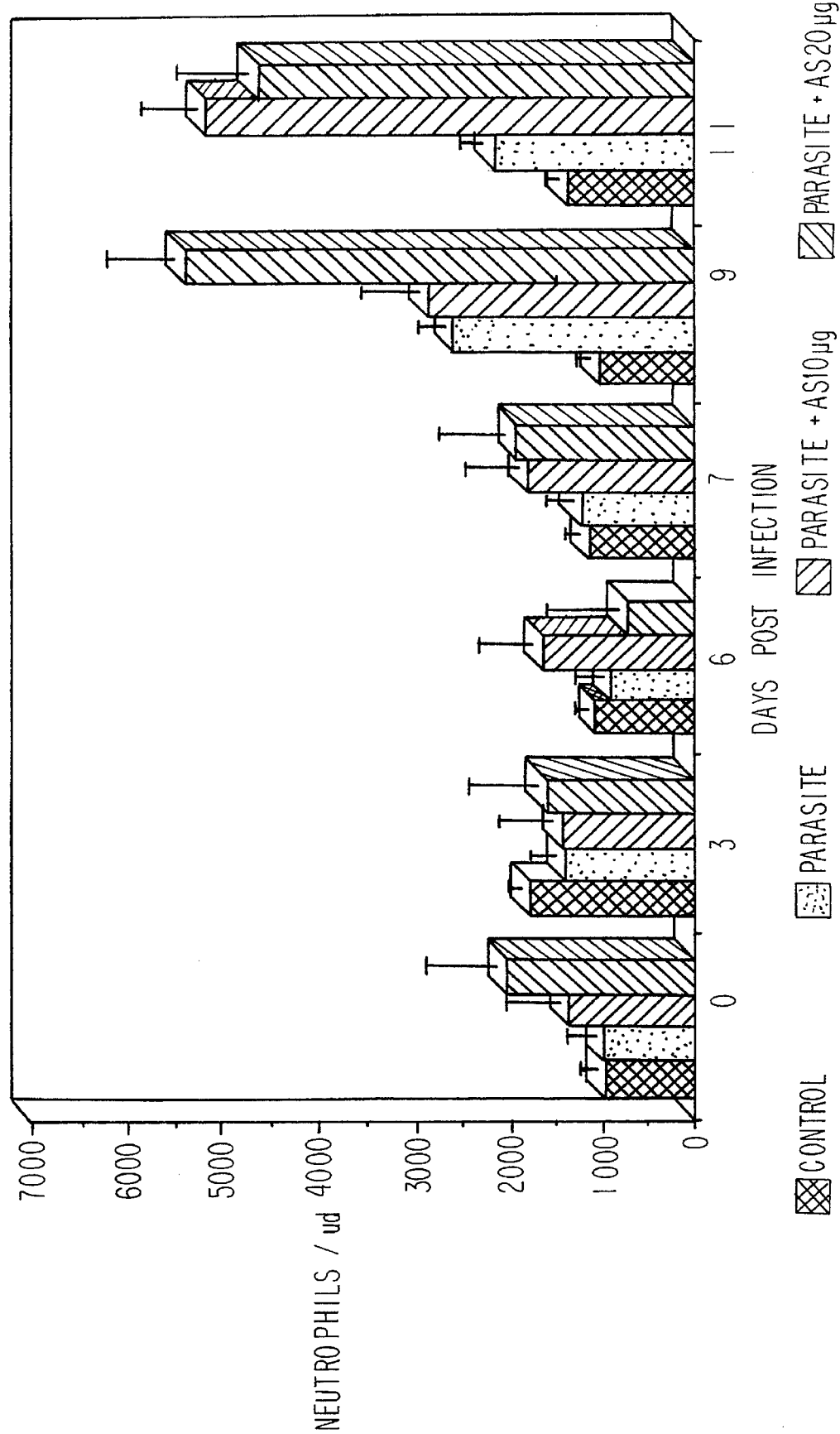

METHOD OF TREATING BABESIOSIS

BACKGROUND OF THE INVENTION

Babesiosis is a term that is used to describe a group of diseases of which are caused by a obligate intraerythrocytic tickborne protozoan parasite of the genus Babesia. Babesiosis occurs in humans and domestic and feral animals. It is a significant disease problem in domestic and wild animals in their natural habitat or in confinement. These animals include cattle, dogs, swine, horses, sheep, goats and foxes wherever significant tick vectors occur. The disease is characterized by anemia, fever and hemoglobinemia. In its acute state, the disease can be fatal. The most important economic losses are caused in cattle by *B. bovis* and *B. bigemina* which act together or singly in the same group of animals although more than 70 species of Babesia have been recognized. *B. rodhani* infected mice are recognized as a model for the study of babesiosis infections.

The treatment of babesiosis has been based on the use of chemotherapeutic agents such as phenamidine isethionate, amicarbalide di-isethionate, imidocarb diproprionate, and diminazene aceturate, tetracyclines or a combination of clindamycin and quinine. Vaccines have been prepared from strains of *B.bovis* and *B. bigemina* by attenuation through splenectomized calves which have been used to immunize cattle.

BRIEF DESCRIPTION OF THE DRAWINGS

FIG. 1 shows the effect of a particular tellurium compound on nitric oxide secretion.

FIG. 2a shows the relation of the severity of the induced parisitemia as measured in red blood cells in relation to the dilution of the inoculum of which contained the parisites.

FIG. 3a shows the dose dependent effects of ammonium trichloro (O.O'-dioxoethylene) tellurate on *B. rodhani* as measured in red blood cells.

FIG. 4a shows the the effect of prior dosing (24 hours; 2 weeks and 1 month) of the ammonium trichloro (O,O'-dioxoethylene) tellurate as measured in red blood cells.

FIG. 4b shows the the effect of prior dosing (24 hours; 2 weeks and 1 month) of the ammonium trichloro (O,O'-dioxoethylene) tellurate as measured percent survival.

FIG. 6 shows the effect of ammonium trichloro (O,O'-dioxoethylene) tellurate on neutrophils.

SUMMARY OF INVENTION

Figure 2B:
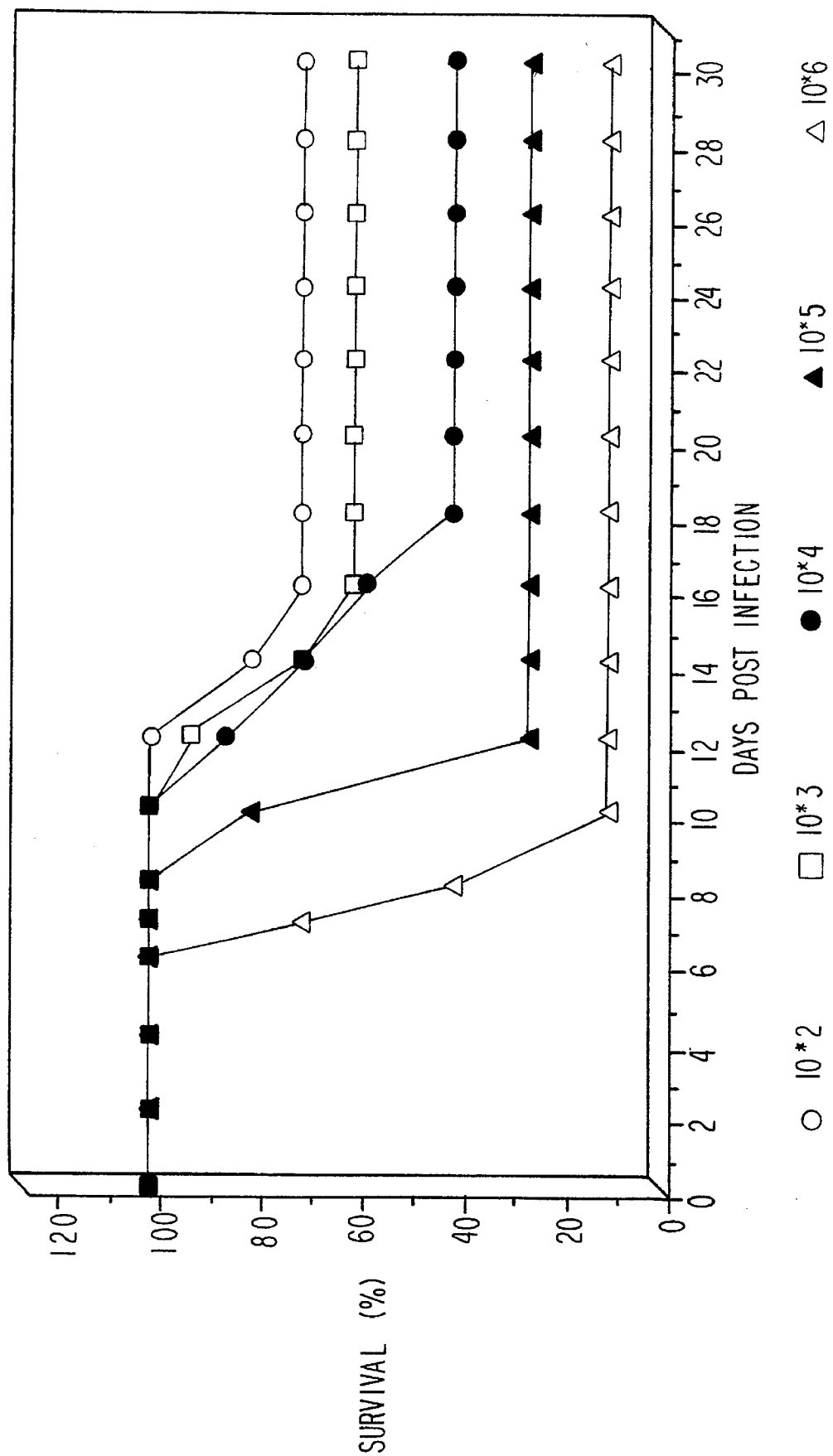
FIG. 2b shows the relation of the severity of the induced parisitemia as measured in percent survival in relation to the dilution of the inoculum of which contained the parisites.

The present invention provides a novel prophylactic and theraputic treatment for babesiosis which is based on the administration of an effective amount of a tellurium compound which stimulates the production of cytokines.

DETAILED DESCRIPTION OF THE INVENTION

The tellurium compounds for use in the invention include those of the formula:

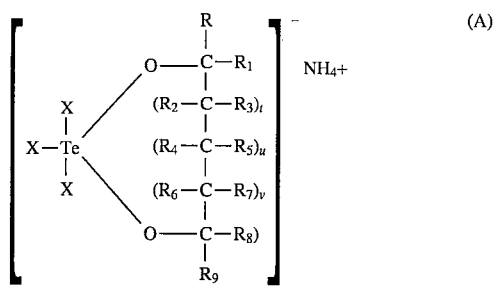
(A)

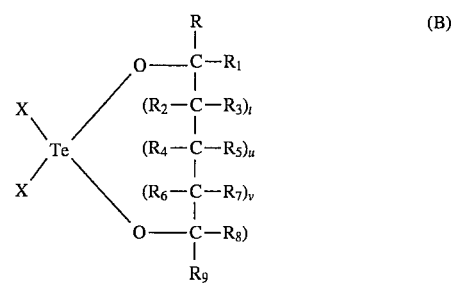
(B)

or

TeO$_2$ or complexes of TeO$_2$ (C)

or

PhTeCl$_3$ (D)

or

TeX$_4$, when X is Cl, Br or F or $(C_6H_5)_4P+(TeCl_3(O_2C_2H_4))-$ (E)

wherein t is 1 or 0; u is 1 or 0; v is 1 or 0; R, R$_1$, R$_2$, R$_3$, R$_4$, R$_5$, R$_6$, R$_7$, R$_8$, and R$_9$ are the same or different and are independently selected from the group consisting of hydrogen, hydroxyalkyl of 1 to 5 carbons, hydroxy, alkyl or from 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —COR$_{10}$ wherein R$_{10}$ is alkyl of 1 to 5 carbons; and X is halogen; while the ammonium salt is illustrated, it is understood that other pharmaceutically acceptable salts such as K+ are within the scope of the invention. The compounds with the five membered rings are preferred.

As used herein and in the appended claims, the term alkyl of 1 to 5 carbon atoms includes straight and branched chain alkyl groups such as methyl; ethyl; n-propyl; n-butyl, and the like; the term hydroxyalkyl of 1 to 5 carbon atoms includes hydroxymethyl; hydroxyethyl; hydroxy-n-butyl; the term halkoakyl of 1 to 5 carbon atoms includes chloromethyl; 2-iodoethyl; 4-bromo-n-butyl; iodoethyl; 4-bromo-n-pentyl and the like; the term alkanoyloxy of 1 to 5 carbon atoms includes acetyl, propionyl, butanoyl and the like; the term carboxyalkyl includes carboxymethyl, carboxyethyl, ethylenecarboxy and the like; the term alkylcarbonylalkyl includes methanoylmethyl, ethanoylethyl and the like; the term amidoalkyl includes —$CH_2CONH_2$; —$CH_2CH_2CONH_2$; —$CH_2CH_2CH_2CONH_2$ and the like; the term cyanoalkyl includes —$CH_2CN$; —$CH_2CH_2CN$; —$CH_2CH_2CH_2CN$ and the like; the alkoxy, of 1 to 5 carbon atoms includes methoxy, ethoxy, n-propoxy, n-pentoxy and the like; the terms halo and halogen are used to signify chloro, bromo, iodo and fluoro; the term acyl includes $R_{16}CO$ wherein $R_{16}$ is H or alkyl of 1 to 5 carbons such as methanoyl, ethanoyl and the like; the term aryl includes phenyl, alkylphenyl and naphthyl; the term N-monoalkylamidoalkyl includes —$CH_2CH_2CONHCH_3$, —$CH_2CONHCH_2CH_3$; the term N,N-dialkylamidoalkyl includes —$CH_2CON(CH_3)_2$; $CH_2CH_2CON(CH_2$—$CH_3)_2$. The tellurium based compounds that are preferred include those of the formula:

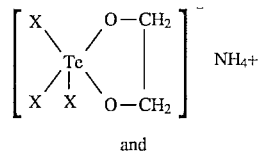

and

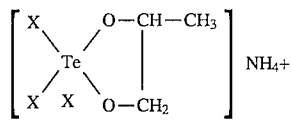

wherein X is halogen. The preferred halogen species is chloro.

Other compounds which are based on tellurium and may be used in the practice of the invention include $PhTeCl_3$, $TeO_2$ and $TeX_4$ $(C_6H_5)_4P^+(TeCl_3(O_2C_2H_4))^-$ (Z. Naturforsh, 36, 307–312 (1981). Compounds of the following structure are also included:

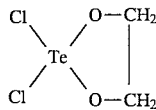

Other compounds useful for the practice of invention include:

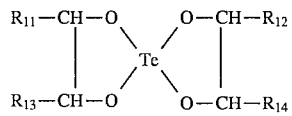

wherein $R_{11}$, $R_{12}$, $R_{13}$ and $R_{14}$ are independently selected from the group consisting of hydrogen, hydroxy-alkyl of 1–5 carbons atoms, hydroxy and alkyl of 1–5 carbons atoms.

Useful dihydroxy compounds for use in the preparation of compounds of structure A or B, include those of formula I wherein R, $R_1$, $R_4$ and $R_5$ are as shown in the Table:

TABLE $$\text{HO}-\underset{R_1}{\underset{|}{\overset{R}{\overset{|}{C}}}}-\underset{R_5}{\underset{|}{\overset{R_4}{\overset{|}{C}}}}-\text{OH} \quad (I)$$

| R | $R_1$ | $R_4$ | $R_5$ |
|---|---|---|---|
| H | H | H | H |
| H | Cl | H | H |
| H | $OCH_3$ | H | H |
| H | $COOCH_3$ | H | H |
| H | H | CN | H |
| H | CHO | H | H |
| H | H | COOH | H |
| H | $CH_2COOH$ | H | H |
| H | H | $CH_2COOCH_3$ | H |
| H | I | H | H |
| H | H | Br | H |
| H | H | $CONH_2$ | H |
| H | H | $CH_2OH$ | H |
| H | COOH | H | H |

Other dihydroxy compounds for use in the preparation of compounds A and B include those of formula II wherein R, $R_1$, $R_2$, $R_3$, $R_4$ and $R_5$ are as shown in the Table:

$$\text{HO}-\underset{R_1}{\underset{|}{\overset{R}{\overset{|}{C}}}}-\underset{R_3}{\underset{|}{\overset{R_2}{\overset{|}{C}}}}-\underset{R_5}{\underset{|}{\overset{R_4}{\overset{|}{C}}}}-\text{OH} \quad (II)$$

| R | $R_1$ | $R_2$ | $R_3$ | $R_4$ | $R_5$ |
|---|---|---|---|---|---|
| H | H | H | H | H | H |
| H | H | Cl | H | H | H |
| H | $CH_2OH$ | H | H | H | H |
| H | H | OH | H | H | H |
| H | H | H | $CH_3$ | H | H |
| H | H | H | $CH_2Cl$ | H | H |
| H | H | H | COOH | H | H |
| H | H | H | $CH_2COOH$ | H | H |
| H | H | H | CHO | H | H |
| H | H | H | H | H | $CH_2CHO$ |
| H | H | $CONH_2$ | H | $H_2$ | $CH_3$ |
| H | H | H | CN | H | H |
| H | H | H | H | $CH_2COHN_2$ | H |
| H | H | H | $COOCH_3$ | $H_3$ | H |
| H | $H_3$ | $OCH_3$ | H | H | H |

Other dihydroxy compounds for use in making compound of formula A and B include those of formula III wherein R, $R_1$, $R_2$, $R_3$, $R_4$ and $R_5$ are as shown in the Table.

$$\text{HO}-\underset{R_1}{\underset{|}{\overset{R}{\overset{|}{C}}}}-\underset{R_3}{\underset{|}{\overset{R_2}{\overset{|}{C}}}}-\underset{R_5}{\underset{|}{\overset{R_4}{\overset{|}{C}}}}-\underset{R_9}{\underset{|}{\overset{R_8}{\overset{|}{C}}}}-\text{OH} \quad (III)$$

| R | $R_1$ | $R_2$ | $R_3$ | $R_4$ | $R_5$ | $R_8$ | $R_9$ |
|---|---|---|---|---|---|---|---|
| H | H | H | H | H | H | H | H |
| H | H | Cl | H | H | H | H | H |
| H | H | H | H | Br | H | H | H |
| H | H | $OCH_3$ | H | H | H | H | H |
| H | H | $CONH_2$ | H | H | H | H | H |
| H | Br | H | H | H | H | H | H |
| H | H | H | H | $CH_2COOH$ | H | H | H |
| H | H | Cl | Cl | H | H | H | H |
| H | $CH_2COOH$ | H | H | H | H | H | H |
| H | $CH_3$ | H | H | H | H | H | H |
| H | $CH_2Cl$ | H | H | H | H | H | H |

-continued

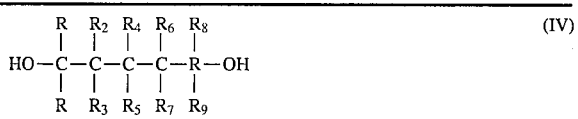

| R | $R_1$ | $R_2$ | $R_3$ | $R_4$ | $R_5$ | $R_8$ | $R_9$ |
|---|---|---|---|---|---|---|---|
| H | H | H | I | H | H | H | H |
| H | $CH_2CN$ | H | H | H | H | H | H |
| H | H | H | H | $CH_2CH_2OH$ | H | H | H |

Additional dihydroxy compounds include those of formula IV wherein R, $R_1$, $R_2$, $R_3$, $R_4$ and $R_5$ are as shown in the Table.

$$\underset{\begin{array}{ccccc}R & R_3 & R_5 & R_7 & R_9\end{array}}{\overset{\begin{array}{ccccc}R & R_2 & R_4 & R_6 & R_8\end{array}}{HO-C-C-C-C-R-OH}} \quad (IV)$$

| R | $R_1$ | $R_2$ | $R_3$ | $R_4$ | $R_5$ | $R_6$ | $R_7$ | $R_8$ | $R_9$ |
|---|---|---|---|---|---|---|---|---|---|
| H | H | H | H | H | H | H | H | H | H |
| H | H | Cl | H | H | H | Cl | H | H | H |
| H | H | Cl | Cl | H | H | H | H | H | H |
| H | H | $CONCH_3$ | H | H | H | Br | H | H | H |
| H | H | Br | H | H | H | $CON(CH_3)_2$ | H | H | H |
| H | H | H | $OCH_3$ | H | H | H | H | H | H |
| H | H | H | H | $OCH_3$ | H | H | H | H | H |
| H | H | H | H | $CH_2COOH$ | H | H | H | H | H |
| H | H | COOH | H | H | H | H | H | H | H |
| H | $CH_3$ | H | H | H | H | H | H | H | H |
| $CH_3$ | H | H | H | H | $CH_3$ | H | H | H | H |
| H | $CH_2CH_3$ | H | H | H | H | H | Cl | H | H |
| H | $CH_2CN$ | H | H | $CH_2OH$ | H | H | H | H | H |
| H | H | H | I | H | H | H | H | CN | H |
| H | $CH_2CH_2COOH$ | H | H | H | H | H | H | H | H |
| H | H | CHO | H | H | H | H | H | H | H |
| H | H | H | F | H | H | H | H | H | H |

Compounds of the following formula are also included:

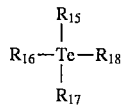

herein $R_{15}$, $R_{16}$, $R_{17}$ and $R_{18}$ are independently selected from halogen, alkyl of 1–5 carbons; aryl, acyl of 1–5 carbon hydroxyalkyl of 1–5 carbons and aminoalkyl of 1–5 carbons may be made by reacting the appropriate di, tri or tetrahaloselenide or telluride with the appropriate hydroxy compound which may be of the formula: $HO-R_{19}$; wherein $R_{19}$; is alkyl of 1 to 5 carbons, haloalkyl of 1 to 5 carbons, aryl, alkylaryl, alkylamido of 1 to 5 carbons, alkylcarbonyl of 1 to 5 carbons, cyanoalkyl of 1 to 5 carbons, cyanoalkyl of 1 to 5 carbons, and an alkoxyalkyl of 2 to 10 carbons. Specific examples of $R_{16}$ include methyl, ethyl, n-propyl, phenyl, tolyl, amidoethyl, cyanomethyl, methyloxymethyl and $CH_2CH_2COOH$.

These compounds are described in U.S. Pat. No. 4,761,490 which is incorporated by reference. In addition, $TeCl_4$; $TeBr_4$ and compounds which give in aqueous solution $TeO_2$ preferably in the form of a complex such as for example $TeO_2$ complex with citric acid or ethylene glycol.

For the prevention and treatment of babesiosis, the tellurium compound may be administered by the oral, intramuscular, intravenous, transdermal or intraperitoneal route to mammals including humans. The oral dose will be 0.15 to 0.5 mg/kg of body weight daily and preferably from 0.03 to 0.1 mg/kg of body weight daily in one dose or in divided doses. The parenteral dose will be 0.03 to 0.2 mg/kg of body weight daily and preferably from 0.006 to 0.02 mg/kg daily given as a bolus injection or as a continuous parenteral infusion.

The invention also includes the prevention of babesiosis or the inducement of a protective effect against infection caused by babesia by the administration by the oral, intramuscular, intravenous, transdermal or intraperitoneal route to mammals including humans, of an effective amount of a tellurium compound which is sufficient to prevent the symptoms of babesiosis when a mammal is exposed to babesia. Generally, this dose is the same dose that is used for the treatment of babesiosis except that the dose of the particular compound is administered to healthy subjects prior to exposure to infection. It is contemplated that the prevention of treatment will be best achieved by administering the compound from about 1 to 8 weeks and preferably about 2 to 4 weeks or more prior to exposure to babesia.

The tellurium compound may be administered prior to or in combination with any of the chemotherapeutic agents conventionally employed in the treatment of babesiosis.

DESCRIPTION OF THE PREFERRED EMBODIMENTS

EXAMPLE 1

Male BALB/c mice, 6–8 weeks old were purchased from the Ani-Lab Laboratories, Israel. The compound, ammonium trichloro (O,O'-dioxoethylene tellurate), was administered to the mice by I.P. injection, every other day, at concentrations of 5, 10, and 20 µg/ml/injection at 24 hours, 2 weeks and 1 month before mice are inoculated with parasites. The vehicle was PBS which is a phosphate saline buffer solution described in U.S. Pat. No. 4,761,490, which is incorporated by reference. The vehicle was use as the control at a dose of 0.2 ml.

A reference population of *B. rodhaini* strain was stored at −80° C. in 15% final concentration of dimethyl sulfoxide. Before the first experiment, the staleiate was quickly thawed and passed twice through mice. Subsequently, every 4 to 5 days, before peak parasitemia, infected red blood cells (IRBC) were further injected i.p. into healthy mice. Before infection, usually one infected mouse was either anesthetized and bled from the retro-orbital sinus without causing injury to the eye by means of a small diameter heparinized micropipette (Brumond Scientific Co., Broomall, Pa. An inoculum of $10^5$ parasites were administered throughout the experiment.

Thin blood smears obtained from minimal tail cuttings, methanol fixed and Giemsa stained were taken every other day throughout the experiments.

Peritoneal exudate macrophages were isolated by peritoneal lavage 4 days after I.P. injection of 2 ml of sterile 3% thioglycolate broth. For nitric oxide secretion studies, cells were suspended in Earle's Medium without phenol red supplemented with 10% fetal calf serum and 1% Pen-strp (Biolab, Israel). Cells were washed and plated at a concentration of $2\times10^5$ cells/ml. After 1–2 hours of incubation (37° C., 5% $CO_2$) in microplates, the nonadherent cells were removed.

Macrophage secretion of nitric oxide into culture supernatants was determined by measuring nitrite as described by Stuehr & Marietta, Proc. Nat. Acad. Sci. 82:7738–7742 (1985). Nitrite concentration in the culture supernatants media was assayed 48 hours after macrophage activation with or without 0.1 or 0.5 µg/ml of ammonium trichloro (O,O'-dioxoethylene tellurate) in PBS. The assay was carried out by a standard Griess reaction. Briefly, 100 µl of samples in triplicates was added to the 96 well plates in a mixture of 1:1 of Griess reagent (1 part of N-[naphthyl] ethylenediamine dihydrochloride and 1 part 1% sulfanilamide in 5% $H_3PO_4$) and absorbance at 550 nm was measured. Total nitrites were determined by comparison to a $NaNO_2$ (1 to 20 µM) standard curve.

Peripheral blood was drawn from mice treated with one of the three concentrations of ammonium trichloro (O,O'-dioxoethylene tellurate): 5, 10 or 20 µg/0.2 ml/mouse in PBS for 2 weeks (every other day) prior to parasite infection. The absolute number of neutrophils was calculated as the percentage of the total of white blood cells (WBC). The total WBC was monitored automatically while the neutrophils were evaluated by the Giemsa-stained thin blood smears.

The results of the tests were analyzed by t-test. Survival curves were tested both by comparing the cumulative percentage of survival for the whole course of infection by the Wilcoxon test and the percentage of survival at the termination of the trial by the Fisher test (2 tailed).

It was found that ammonium trichloro (O,O'-dioxoethylene tellurate) induces the secretion in vitro of large amounts of NO from mice macrophages. The secretion was analyzed in peritoneal exudate cells from BALB/c mice injected with thioglycolate. FIG. 1 shows that ammonium trichloro (O,O'-dioxoethylene tellurate) at 0.1 µg/ml induced the secretion of very large amounts of nitric oxide (18 µM compared to 1.25 µM of control, and at 0.5 µg/ml P<0.01) smaller amounts of nitric oxide that were still significantly higher than from the control (6.25 compared to 1.25 µM, respectively, P<0.05).

The optimal infective dose of B. rodhani in mice was determined by inoculating each mouse with 10 fold dilutions of IRBC containing from $10_6$ to $10_2$IRBC. FIG. 2 shows that the severity of the parasitemia was generally related to the dilution of the inoculum. Peak parasitemia (95%) was reached on day 8 for the $10_6$ inoculum. The survival rate ranged from 10% to 70% for the highest and lowest inocula respectively with mice beginning to die around days 7–8 ($10_6$ and $10_5$ inocula) and on days 12–14 for the lower inocula. As a result of this titration an inoculum of $10_5$ IRBC per mouse was chosen as the standard infection dose for testing the effectiveness of the method of the present invention.

Figure 3B:
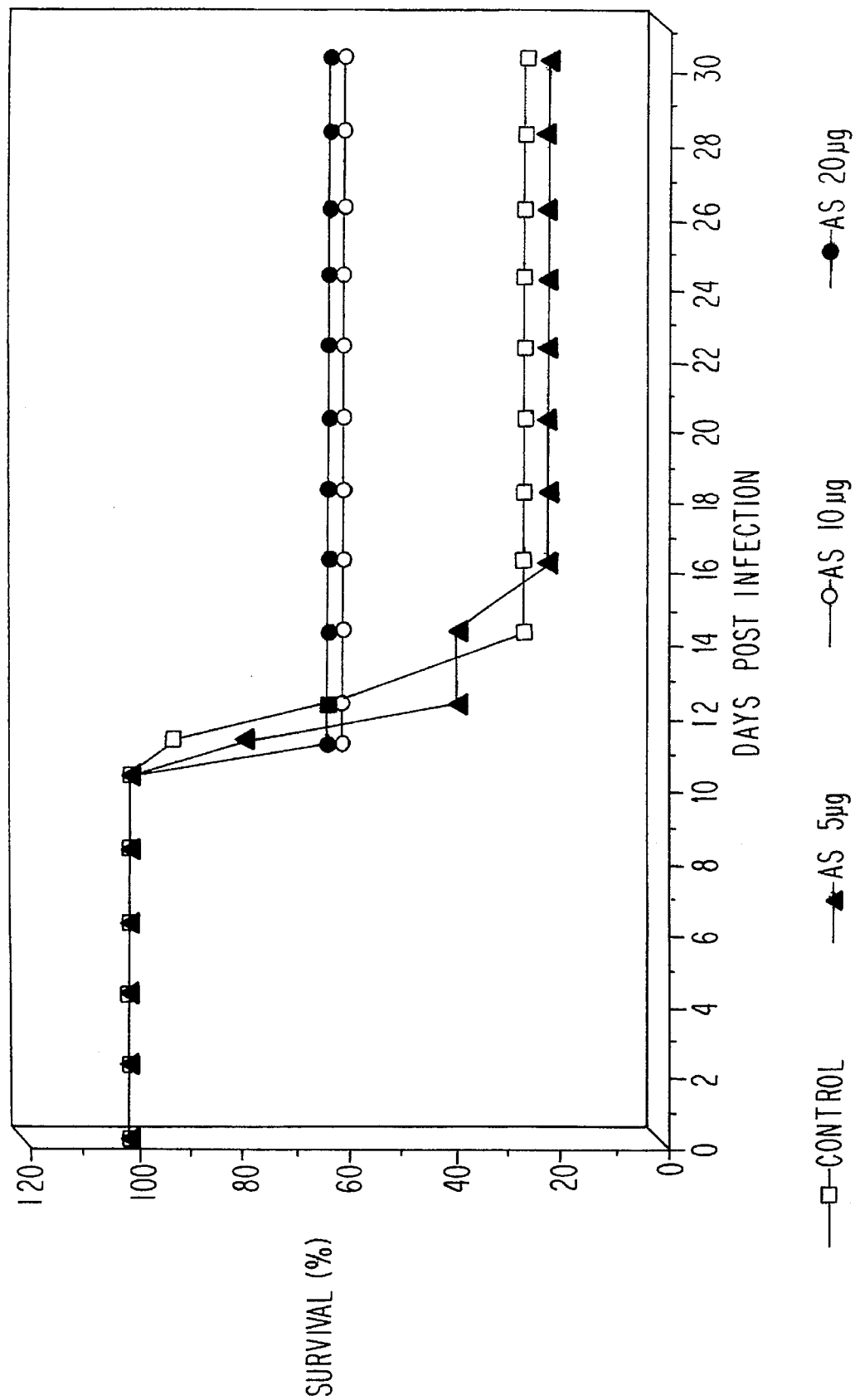
FIG. 3b shows the dose dependent effects of ammonium trichloro (O.O'-dioxoethylene) tellurate on *B. rodhani* as measured in percent survival.

The effect of the compound ammonium trichloro (O,O'-dioxoethylene tellurate) on B. rodhani infected mice was determined by injecting 5 µg, 10 µg or 20 µg (per mouse) of the compound IP in PBS. FIG. 3a shows that when this compound was administered in different concentrations for 2 weeks (every other day) before injecting parasites, only the 10 µg and the 20 µg concentrations caused a significant decrease in the parasitemia on the 8th and on the 12th day (for example 22% for the 10 µg and 35% for the 20 µg vs. 42% IRBC in the control group at day 8) in contrast to the 5 µg concentration at which no difference was observed compared to the control (50% vs. 42% at day 8 respectively). Survival was significantly higher in the 10 and 20 µg treated groups than in the 5 µg and control groups (65% (p<0.05) and 67% (p<0.01) respectively. 22% and 25% (p<0.08) respectively. These results show the influence of ammonium trichloro (O,O'-dioxoethylene tellurate) on the course of parasitemia and that the survival rate is dose dependent.

FIG. 4a shows the effect of the administration of 10 µg of ammonium trichloro (O,O'-dioxoethylene tellurate) which is administered 24 hours prior to parasite infection. No difference was observed in the course of parasitemia or the survival rate (FIG. 4b) compared to control mice. In contrast, when ammonium trichloro (O,O'-dioxoethylene tellurate) was injected 2 weeks before parasite infection, on the 8th day, there was a significant decrease in parasitemia (from 45% IRBC for the 10 µg-24h pre-infection of ammonium trichloro (O,O'-dioxoethylene tellurate) to 20% IRBC in the 2 week before treatment). Moreover, when administering the ammonium trichloro (O,O'-dioxoethylene tellurate) 1 month prior to parasite infection, a significant decrease in parasitemia was observed on the 8th day (reaching maximal parasitemia of 18.4%) as well as on the 12th day (17% for the 1 month prior administration of ammonium trichloro (O,O'-dioxoethylene tellurate) compared to the control with 42% and 56% on days 8 and 12 respectively, p<0.05). A significant improvement in survival rate was also observed (62.5% and 60% vs. 27% in controls p<0.05).

Figure 5A:
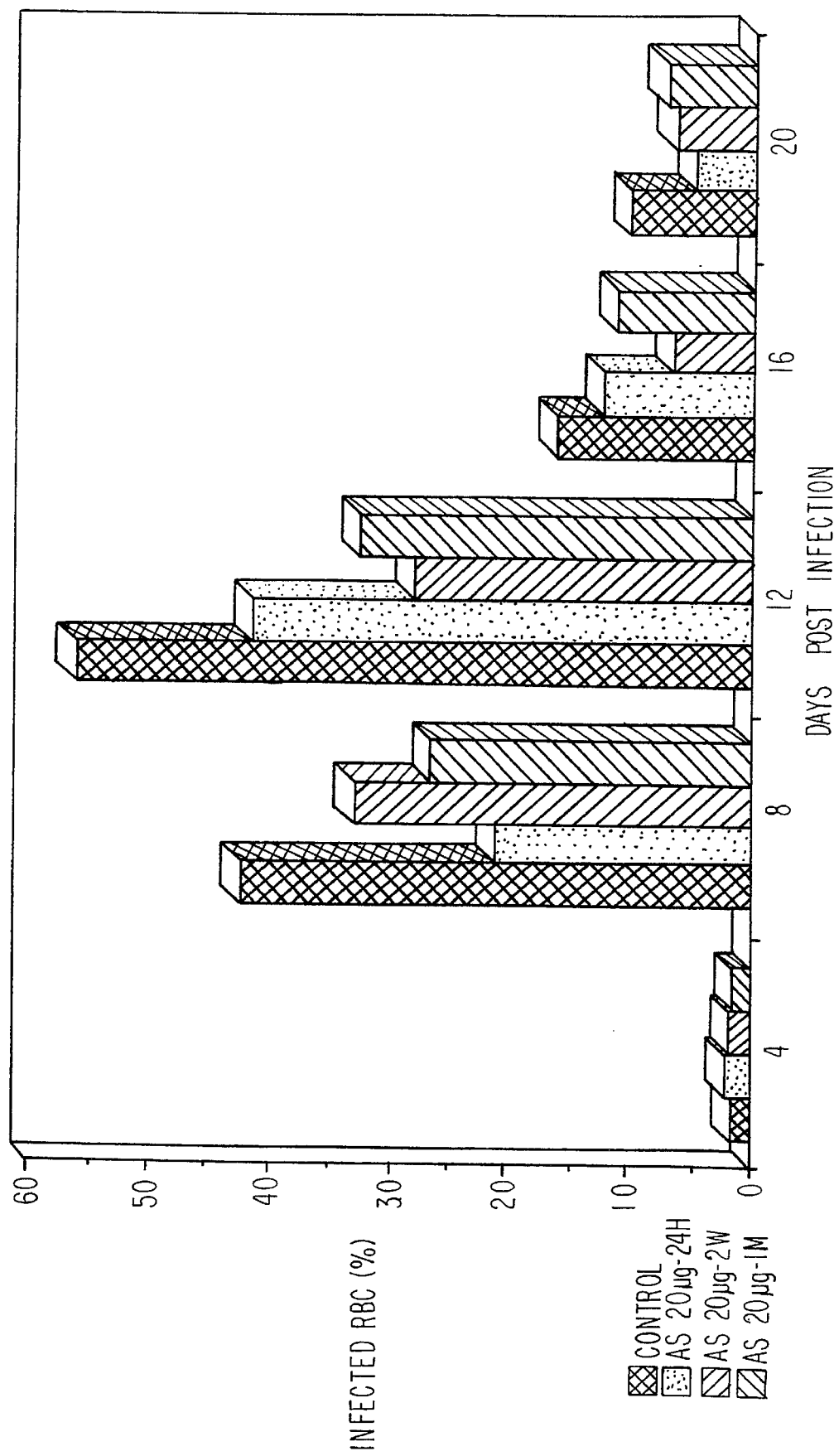
FIG. 5a shows the the effect of prior dosing (24 hours; 2 weeks and 1 month) of the ammonium trichloro (O,O'-dioxoethylene) tellurate as measured in red blood cells.
Figure 5B:
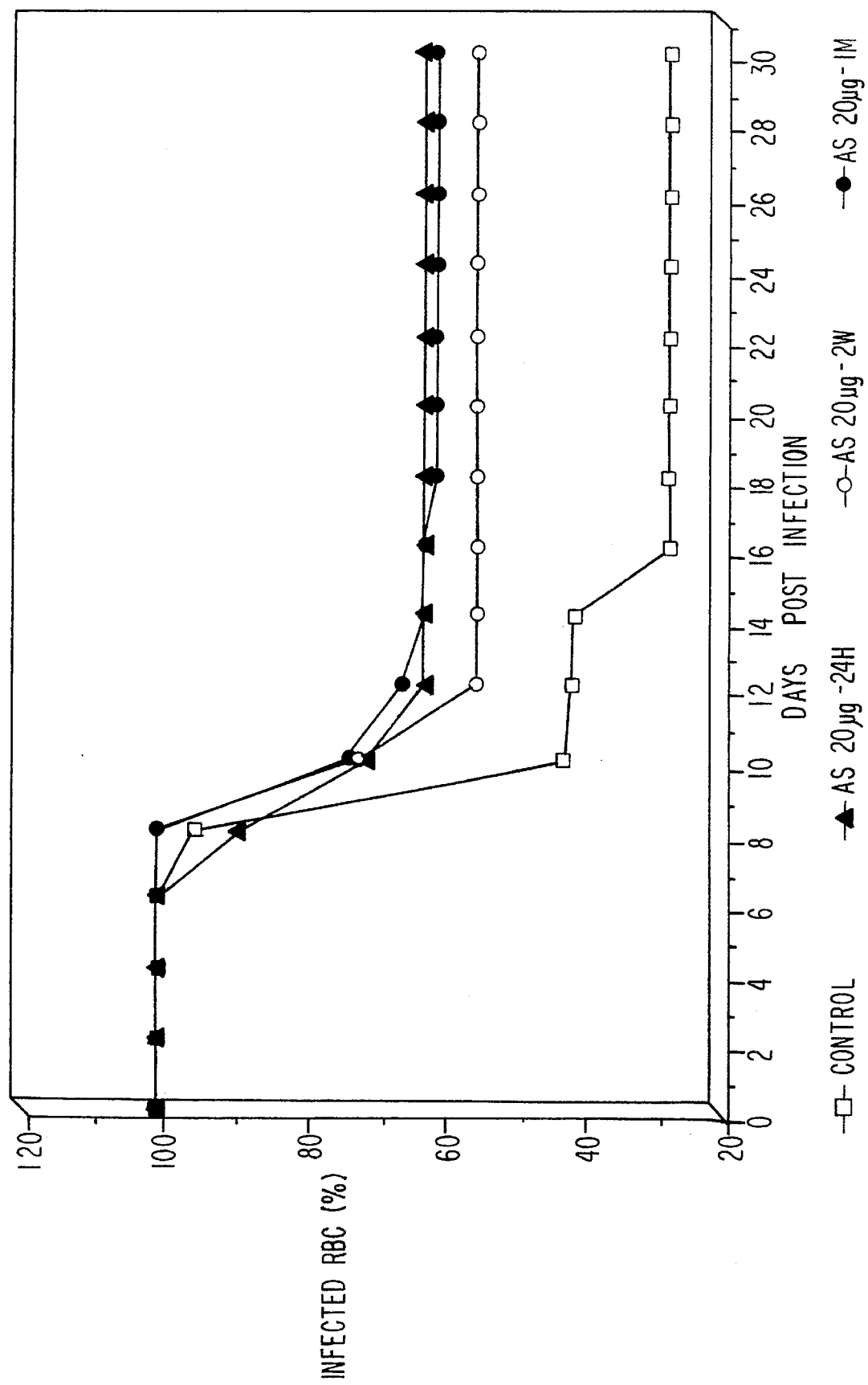
FIG. 5b shows the the effect of prior dosing (24 hours; 2 weeks and 1 month) of the ammonium trichloro (O,O'-dioxoethylene) tellurate as measured in percent survival.

FIG. 5a shows the effect of the administration of 20 µg of ammonium trichloro (O,O'-dioxoethylene tellurate) 24h, 2 weeks and 1 month before parasite infection. A decrease in parasitemia occurred for the 24 h protocol on the 8th day (21%, 33% and 26.5% respectively compared to the control; on the 12th day 41.5%, 28% and 32.5% respectively compared to control. There was also an increase in survival rates (62% for 24 h administration, 54.2% for 2 week administration and 60% for 1 month administration compared to 27% for the control as shown in FIG. 5b.

The effect of ammonium trichloro (O,O'-dioxoethylene tellurate) on neutrophils is shown in FIG. 6. The administration of 10 µg and 20 µg of ammonium trichloro (O,O'-dioxoethylene tellurate) 2 weeks before parasite infection caused a significant increase in the number of neutrophils on the 11th day after the infection (2825 and 5335) compared to the control which exhibited 995 neutrophils/µl p<0.05) The administration of 20 µg of ammonium trichloro (O,O'-dioxoethylene tellurate) resulted in a significant increase in neutrophils on days 9 and 11 as well in mice which were not given parasites (control)(4587 neutrophils vs. 1327 neutrophils)

The suppressive effect of ammonium trichloro (O,O'-dioxoethylene tellurate) on B. rodhaini mice was demonstrated by the morphology of the RBCs and WBCs in blood smears.

Many variations in the present invention will suggest themselves to those skilled in the art in light of the above, detailed description. All such obvious modifications are within the full intended scope of the appended claims.

We claim:

1. A method for treating or preventing babesiosis which comprises administering to a host that is in need of treatment or is susceptible to babesiosis an effective amount, for the treatment or prevention of babesiosis, of a tellurium compound of the formula:

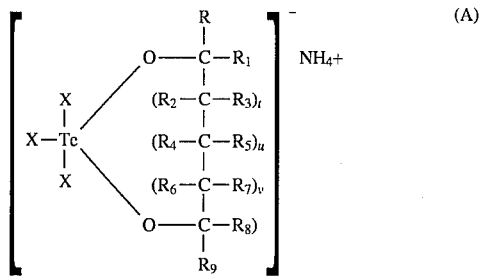 (A)

or

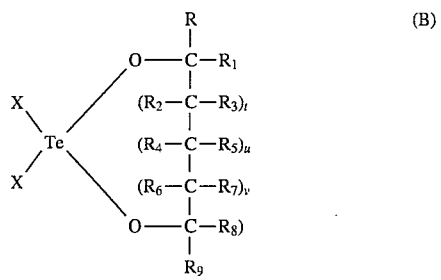 (B)

or

TeO$_2$ or complexes of TeO$_2$ or

PhTeCl$_3$ (D)

or $(C_6H_5)_4P+(TeCl_3(O_2C_2H_4))-$

TeX$_4$, wherein t is 1 or 0; u is 1 or 0; v is 1 or 0; R, $R_1$, $R_2$, $R_3$, $R_4$, $R_5$, $R_6$, $R_7$, $R_8$, and $R_9$ are the same or different and are independently selected from the group consisting of hydrogen, hydroxyalkyl of 1 to 5 carbons, hydroxy, alkyl of 1 to 5 carbon atoms, halogen, haloalkyl of 1 to 5 carbon atoms, carboxy, alkylcarbonylalkyl of 2 to 10 carbons, alkanoyloxy of 1 to 5 carbon atoms, carboxyalkyl of 1 to 5 carbons atoms, acyl, amido, cyano, amidoalkyl of 1 to 5 carbons, N-monoalkylamidoalkyl of 2 to 10 carbons, N,N-dialkylamidoalkyl of 4 to 10 carbons, cyanoalkyl of 1 to 5 carbons alkoxy of 1 to 5 carbon atoms, alkoxyalkyl of 2 to 10 carbon atoms and —COR$_{10}$ wherein R$_{10}$ is alkyl of from 1 to 5 carbons; X is halogen and complexes of said tellurium compound.

2. A method as defined in claim 1 wherein the tellurium compound is administered to a susceptible host to prevent babesiosis.

3. A method as defined in claim 1 wherein the tellurium compound is administered to a host who is afflicted with babesiosis.

4. A method as defined in claim 1 wherein the tellurium compound is ammonium trichloro (O,O'-dioxoethylene tellurate).

5. A method as defined in claim 2 wherein the tellurium compound is ammonium trichloro (O,O'-dioxoethylene tellurate).

6. A method as defined in claim 3 wherein the tellurium compound is ammonium trichloro (O,O'-dioxoethylene tellurate).

7. A method as defined in claim 1 wherein the tellurium compound is administered parenterally.

8. A method as defined in claim 1 wherein the tellurium compound is administered orally.

9. A method as defined in claim 1 wherein tellurium compound is administered to cattle.

10. A method as defined in claim 7 wherein the compound is ammonium trichloro (O,O'-dioxoethylene tellurate).

* * * * *